United States Patent [19]

Agarwala

[11] Patent Number: 4,622,973

[45] Date of Patent: * Nov. 18, 1986

[54] PROGRAMMABLE FUNCTIONAL ELECTRICAL STIMULATION SYSTEM

[75] Inventor: Poonam Agarwala, New Brighton, Minn.

[73] Assignee: Empi, Inc., Fridley, Minn.

[*] Notice: The portion of the term of this patent subsequent to Jul. 16, 2002 has been disclaimed.

[21] Appl. No.: 621,239

[22] Filed: Jun. 15, 1984

[51] Int. Cl.⁴ .................................... A61N 1/36
[52] U.S. Cl. ....................................... 128/421
[58] Field of Search .............. 128/419 R, 421–423, 128/419 PG

[56] References Cited

U.S. PATENT DOCUMENTS

| | | | |
|---|---|---|---|
| 4,165,750 | 8/1979 | Aleev et al. | 128/422 |
| 4,390,023 | 6/1983 | Rise | 128/421 |
| 4,480,830 | 11/1984 | Petrofsky et al. | 128/423 W |
| 4,503,857 | 3/1985 | Boute et al. | 128/419 PG |
| 4,505,275 | 3/1985 | Chen | 128/421 |
| 4,528,984 | 7/1985 | Morawetz et al. | 128/421 |

FOREIGN PATENT DOCUMENTS 3315513 11/1983 Fed. Rep. of Germany ...... 128/421

OTHER PUBLICATIONS

Petrofsky "Sequential Motor Unit Stimulation Through Peripheral Motor Nerves in the Cat" *Med & Biol Eng & Comput* Jan. 1979, 17, 87–93.

Trnkoczy "Present State and Prospects in the Design of Multichannel FES Stimulators For Gait Correction in Paretic Patients" *TITJ Life Sci* 1978, 8: 17–27.

Goovaerts "A Programmable Stimulator for Physiological Applications" *Med & Biol Eng & Comput* Jan. 1975, vol. 13, No. 1, pp. 112–118.

*Primary Examiner*—William E. Kamm
*Assistant Examiner*—Mitchell J. Shein
*Attorney, Agent, or Firm*—Kinney & Lange

[57] ABSTRACT

A muscle stimulator system produces an electrical output pulse train which provides functional electrical stimulation (FES) of muscles or muscle groups. The muscle stimulator system includes a clinical device (which is line powered and independently programmable) and a battery-operated personal device (which can be programmed using the clinical device). In addition, external memory modules are provided to store the FES regimens established in the clinical device during the PROGRAM mode. The clinical device is capable of retrieving the FES regimens from the external memory module. The personal device includes a manually operated amplitude control which provides an amplitude control signal for controlling the amplitude of the output pulse train.

17 Claims, 3 Drawing Figures

PROGRAMMABLE FUNCTIONAL ELECTRICAL STIMULATION SYSTEM

BACKGROUND OF THE INVENTION

1. Field of the Invention

The present invention relates to the electrical stimulation of muscles. In particular, the present invention relates to a programmable muscle stimulator system which establishes, stores and automatically reproduces a desired regimen of functional electrical stimulation.

2. Description of the Prior Art

Functional electrical stimulation (FES), which sometimes in a more restricted sense is called neuromuscular stimulation (NMS), is a technique of causing muscles to contract by means of an electrical current. FES is typically used therapeutically when there is a lack of neuromotor faculty, or when muscles which have been weakened or damaged by disease or trauma can benefit from a program of enforced contractions akin to voluntary exercise. In some cases, FES can be used in lieu of or complementary to exercise to strengthen an athlete's muscles. In addition, FES can be used prosthetically when voluntary motor ability is irretrievably lost, such as in certain forms of paralysis.

Muscle stimulators of various types have been developed to accomplish FES. A typical muscle stimulator consists of an electrical pulse generator and one or two pairs of electrodes (depending upon whether the pulse generator has one or two output channels). The electrodes are placed in appropriate locations on the skin, and electrical pulse trains from the pulse generator are applied transcutaneously to produce a contraction of muscles or groups of muscles. The effectiveness of the contraction is determined visually by the clinician, or by the patient himself.

The typical muscle stimulator of the prior art has controls which allow the clinician or the patient to select a stimulation regimen which is best suited for the particular purpose. In general, the controls permit selection of the pulse repetition rate (i.e. the number of pulses per second) and the pulse intensity (i.e. the amplitude, the pulse width or both). Most muscle stimulators also have a "time on" control which determines a contraction time and a "time off" control which determines a relaxation time. The clinician sets these controls to define a succession of contraction/relaxation cycles which the clinician believes is best for the desired purpose. Normally, the relaxation time is longer than the contraction time. For example, in a typical FES regimen the "time on" control may be set for a contraction time of about ten seconds, and the "time off" control may be set for a relaxation time of about twenty-five seconds.

Most muscle stimulators used for FES also include a "ramp up" control which selects a fraction of the contraction time during which the intensity of the pulses increases gradually. This prevents a sudden shock to the patient at the onset of the contraction time, and makes the contraction more naturally "physiological". In some cases, the muscle stimulator includes both a "ramp up" control and a "ramp down" control so that the slope of the pulse intensity at both the onset and the termination of the contraction time can be selected by the clinician.

When commencing the application of FES for any of the purposes described above, the clinician normally sets the stimulator to a "CONTINUOUS" mode (which is defined as infinite "time on", zero "time off", and no ramp times) and also selects a pulse repetition rate. After placing the electrodes optimally on the patient's skin, the clinician proceeds to cause a contraction to occur by gradually increasing the intensity setting of the intensity control from a zero setting to a setting which produces a maximum contraction. The clinician then determines (by prior knowledge and intuition) suitable "time on", "time off", "ramp up", and "ramp down" settings. Next, the clinician submits the patient to a session at the selected regimen, and observes the effect of that regimen on the patient. Often the clinician adjusts one or more of the control settings and continues to observe the effects on the patient until a desired regimen is achieved. The patient may then be asked to continue sessions at home using the same regimen. This requires that the patient remember all of the control settings and/or make certain that none of the settings are disturbed.

There has been a continuing need for improved muscle stimulators which are easier for both the clinician and the patient to use. In particular, there has been a continuing need for a muscle stimulator that saves the clinician (and the patient) the laborious steps which have been performed in the past in order to arrive at a desired FES regimen.

3. Reference to Copending Application

In U.S. patent application Ser. No. 488,124, filed Apr. 15, 1983 by P. Morawetz (which is assigned to the same assignee as the present application), an improved apparatus for functional electrical stimulation is disclosed which automatically reproduces a desired FES regimen. The apparatus includes means for selecting a PROGRAM mode during which a desired FES regimen is established, and an EXECUTE mode during which the desired FES regimen is reproduced.

During the PROGRAM mode, user-actuated control means controls the intensity of the electrical output signal of the apparatus to produce the desired FES regimen. The apparatus also includes means for periodically sampling a signal representative of the controlled intensity during the PROGRAM mode, and means for storing data based upon the sampled signal.

The FES apparatus of the Morawetz application also includes means for controlling the intensity of the output signal during the EXECUTE mode as a function of the stored data. Since the stored data represents the sampling of the controlled intensity during the PROGRAM mode, the intensity of the output signal during the EXECUTE mode automatically reproduces the desired FES regimen. A desired FES regimen, therefore, is established simply and quickly during the PROGRAM mode, and is automatically reproduced later when the apparatus is in the EXECUTE mode.

SUMMARY OF THE INVENTION

The muscle stimulator system of the present invention includes a clinical device which is used by the clinician in establishing an FES regimen, and a personal device which is programmable by the clinical device and which automatically reproduces the FES regimen which has been received from the clinical device.

In preferred embodiments, the clinical device includes means for selecting a program mode during which a desired FES regimen is established and an execute mode during which the FES regimen is reproduced. The clinical device establishes and stores the desired FES regimen during the program mode based upon inputs which select rate, an on-ramp and an off-ramp time, and an output amplitude.

The personal device is preferably a batterypowered, portable unit which is connectable to the clinical device. Once an FES regimen which has been stored in the clinical device during the program mode is transferred to the personal device, the personal device operates independently of the clinical device, and reproduces the FES regimen. As a result, the personal device is simple, requires fewer components and operator controls, and yet accurately reproduces complex FES regimens which have been established by the clinician using the clinical device.

In preferred embodiments, the system of the present invention also includes an external memory module which is connectable to the clinical device. The external memory module includes means for storing a desired FES regimen which has been established by the clinical device. During a "save" mode, the clinical device transfers the FES regimen to the external memory module. During a "load" mode, a previously stored FES regimen is transferred from the external memory module to the clinical device.

In this preferred embodiment of the present invention, the external memory module allows the clinician to store the FES regimen established for a particular patient in the external memory module, and then use the clinical device for other patients. When the patient returns for further treatment by the clinician, the clinician can reconnect the external memory module which stores the FES regimen for that patient, and reload the regimen into the clinical device. By selecting the execute mode, the clinician can monitor the effects of the FES regimen on the patient as the clinical device reproduces the FES regimen which has been loaded from the external memory module.

DETAILED DESCRIPTION OF THE PREFERRED EMBODIMENTS

Figure 2:
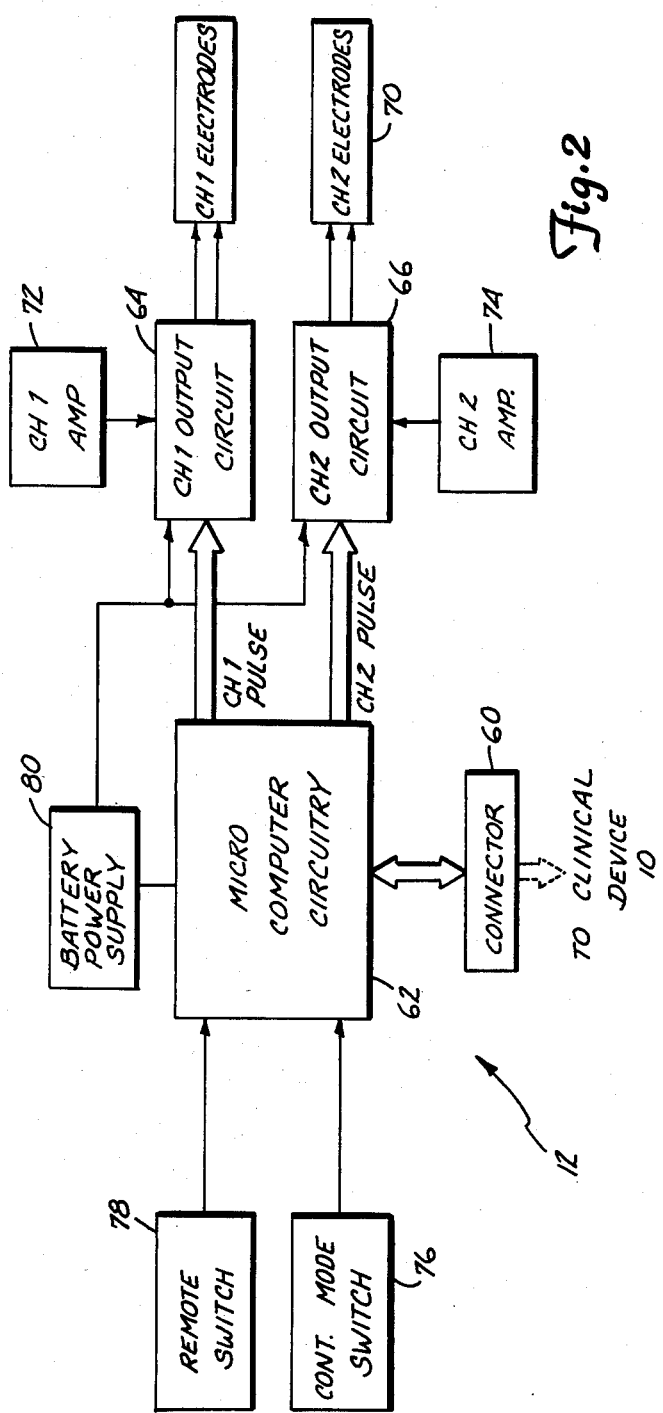
FIG. 2 is an electrical block diagram of a personal device of the FES muscle stimulator system.
Figure 3:
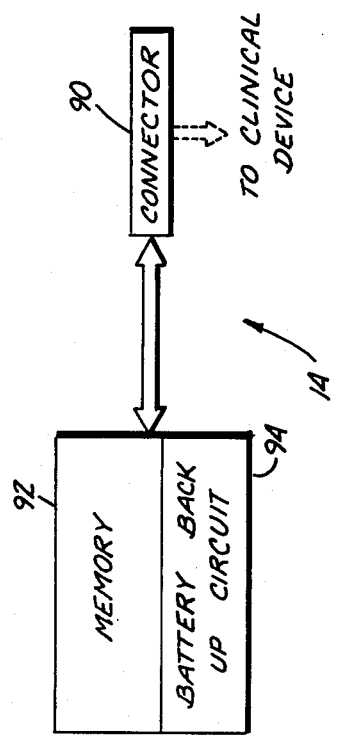
FIG. 3 is an electrical block diagram of an external memory module of the FES muscle stimulator system.

The muscle stimulator system of the present invention preferably includes three separate components: clinical device 10 (FIG. 1), personal device 12 (FIG. 2), and external memory module 14 (FIG. 3). Together, these components provide a system which is easily programmable by the clinician, yet is low cost and simple to use from the patient's standpoint.

Clinical device 10, which is used by the clinician, includes autoprogrammable pulse generation circuit 16, Channel 1 output circuit 18, Channel 2 output circuit 20, Channel 1 electrodes 22, Channel 2 electrodes 24, Rate Select switch 26, Output Type switch 28, Channel 1 Amplitude potentiometer 30, Channel 2 Amplitude potentiometer 32, Continuous Mode switch 34, Remote switch 36, Channel 1 Program/Execute switch 38, Channel 2 Program/Execute switch 40, Phase switch 42, OFF/ON Ratio switch 44, Program Transfer switch 46, Load/Save switch 48, connectors 50 and 52, and faulty transfer annunciator 54.

Autoprogrammable pulse generation circuit 16, which includes a microcomputer and associated circuitry, is preferably similar to the pulse generation circuit described in the previously mentioned copending application by P. Morawetz, and that description is hereby incorporated by reference. Pulse generation circuit 16 produces a CH1 PULSE signal which is supplied to Channel 1 output circuit 18 and a CH2 PULSE signal which is supplied to Channel 2 output circuit 20. The pulse rate of the CH1 PULSE signal and the CH2 PULSE signal is determined by the setting of Rate Select switch 26. In one preferred embodiment, the pulse rate which is selectable by Rate Select switch 26 varies from one pulse per second to ninety-nine pulses per second (i.e. 1 Hz to 99 Hz).

Channel 1 output circuit 18 produces an output pulse train to Channel 1 electrodes 22 as a function of the CH1 PULSE signal and an amplitude control signal (AMP1) from Channel 1 Amplitude potentiometer 30. Similarly, Channel 2 output circuit 20 provides an output pulse train to Channel 2 electrodes 24 as a function of the CH2 PULSE signal and an amplitude control signal (AMP2) from Channel 2 Amplitude potentiometer 32. In the preferred embodiment shown in FIG. 1, the output pulse trains provided by Channel 1 output circuit 18 and Channel 2 output circuit 20 are either monophasic or biphasic, depending upon the setting of Output Type switch 28.

The amplitude of the pulses of the output pulse trains produced by Channel 1 and Channel 2 output circuits 18 and 20 are controlled by Channel 1 Amplitude potentiometer 30 and Channel 2 Amplitude potentiometer 32, respectively. The Channel 1 amplitude control signal (AMP1) is provided to both Channel 1 output circuit 18, and also to pulse generation circuit 16. As discussed in further detail later, the AMP1 signal is used by pulse generation circuit 16 during the PROGRAM mode, in which a desired FES regimen is stored for later use in an EXECUTE mode.

The Channel 2 amplitude control signal (AMP2) from Channel 2 Amplitude potentiometer 32 is supplied to Channel 2 output circuit 20, and also to pulse generation circuit 12. The AMP2 signal controls the amplitude of the output pulse train from Channel 2 output circuit 20, and also is used by pulse generation circuit 16 during the PROGRAM mode to produce a stored FES regimen for Channel 2 which can be replicated when clinical device 10 is in the EXECUTE mode.

Figure 1:
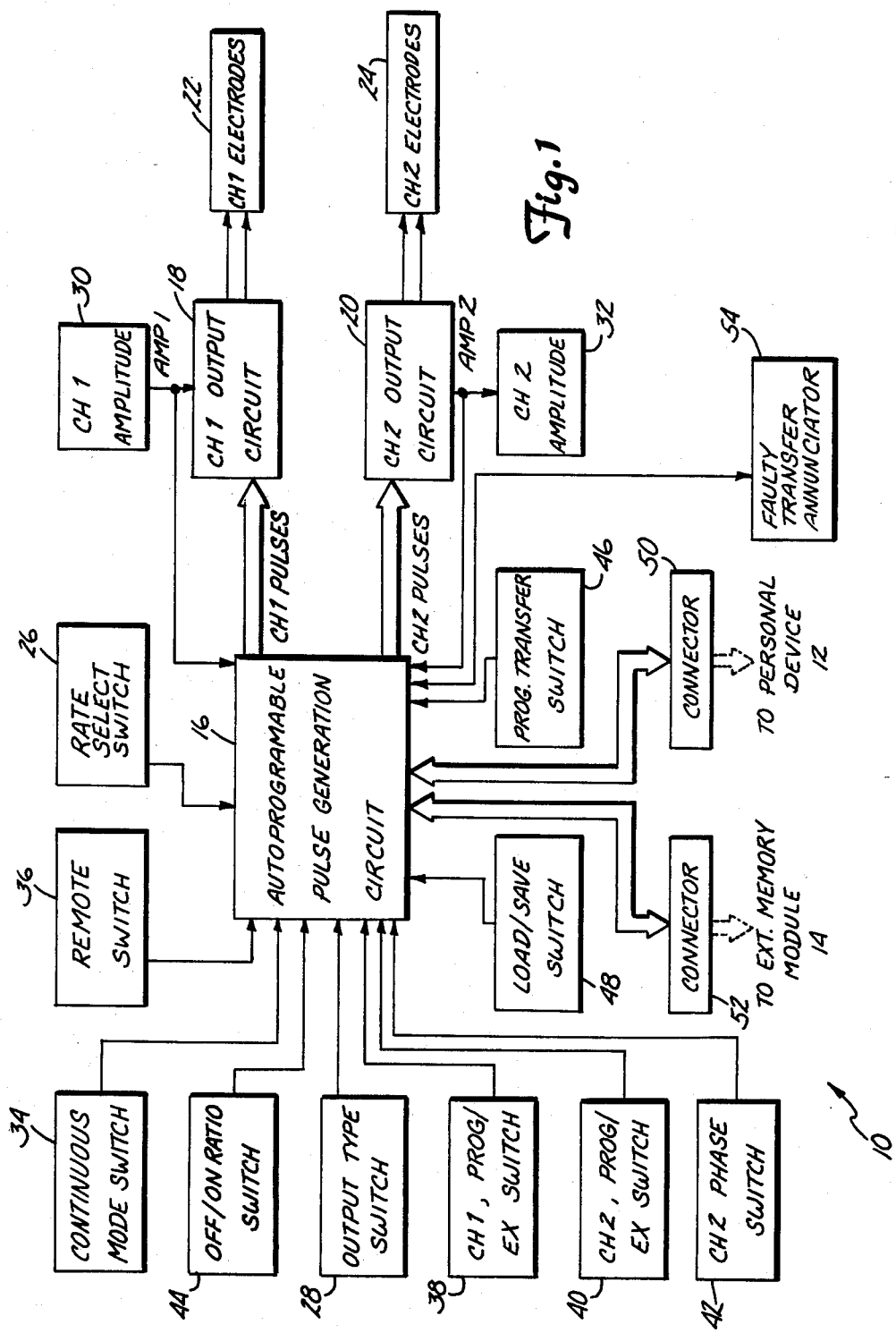
FIG. 1 is an electrical block diagram of a clinical device of the FES muscle stimulator system of the present invention.

The preferred embodiment of muscle stimulator 10 shown in FIG. 1 is capable of operating in several different modes. These modes are, in order of priority: (1) CONTINUOUS mode; (2) REMOTE mode; (3) PROGRAM mode; and (4) EXECUTE mode. There are also several modes which operate on an interrupt basis: TRANSFER, LOAD, and SAVE.

The CONTINUOUS mode is selected whenever Continuous Mode switch 34 is actuated. In the CONTINUOUS mode, output pulse trains are supplied by Channel 1 output circuit 18 and Channel 2 output circuit 20 as a function of the selected rate, output type, and amplitude. The Channel 1 and Channel 2 output pulse trains are in phase and identical in pulse width, but may differ in amplitude based upon the AMP1 and AMP2 control signals from Channel 1 Amplitude potentiometer 30 and the Channel 2 Amplitude potentiometer 32.

The CONTINUOUS mode is primarily used when the clinician is attempting to determine the proper placement of electrodes 22 and 24. In the CONTINUOUS mode, the output pulse trains from output circuits 18 and 20 are continuous (i.e. infinite "time on" and zero "time off").

The REMOTE mode is enabled when Remote switch 36 is actuated. Output pulse trains are produced by Channel 1 output circuit 18 and Channel 2 output circuit 20 as long as Remote switch 36 is actuated. When Remote switch 36 is released by the clinician, the output pulse trains cease.

In the PROGRAM mode, the clinician establishes a desired FES regimen for Channel 1 or for Channel 2. The FES regimen is stored in the form of digital data by pulse generation circuit 16 for later use when clinical device 10 is in the EXECUTE mode.

A desired FES regimen for Channel 1 is established during the PROGRAM mode when Program/Execute switch 38 is in the PROGRAM position. Pulse generation circuit 16 supplies the CH1 PULSE signal to Channel 1 output circuit 18. The CH1 PULSE signal has a repetition rate which is determined by Rate Select switch 26, and has a full pulse width (which in one preferred embodiment is about 235 microseconds).

As long as Channel 1 Amplitude potentiometer 30 is set at its minimum amplitude setting, no output pulses appear at the output of Channel 1 output circuit 18. The clinician then begins to change the setting of Channel 1 Amplitude potentiometer 30 (and thus the AMP1 signal) so that the amplitude of the output pulse train from Channel 1 output circuit 18 changes. Typically, the clinician progressively changes the setting of Channel 1 Amplitude potentiometer 30, so that the amplitude of the output pulse train from Channel 1 output circuit 18 is progressively increased until a desired maximum amplitude is achieved. This represents the "ramp up" portion of the FES regimen. Channel 1 Amplitude potentiometer 30 is then typically maintained at the desired maximum amplitude setting for a period long enough to produce the required muscle contraction. This is equivalent to the "time on" period of the FES regimen. The clinician then changes the setting of Channel 1 Amplitude potentiometer 30 to cause a progressive reduction in the amplitude of the output pulse train from Channel 1 output circuit 14 until the amplitude reaches zero. This represents the "ramp down" portion of the FES regimen.

During the PROGRAM mode, pulse generation circuit 16 periodically samples the AMP1 signal and stores a sequence of digital data based on that sampled information for use during the EXECUTE mode. The sampling rate used by pulse generation circuit 16 is sufficiently high so that the stored digital data accurately represents the variation in the AMP1 signal (and thus the variation in the amplitude of the Channel 1 output pulse train) during the PROGRAM mode. This stored digital data is used later during the EXECUTE mode in reproducing the FES regimen for Channel 1.

When Channel 1 Program/Execute switch 38 is in the PROGRAM position, only a Channel 1 FES regimen can be stored. Channel 2 Program Execute switch 40 is ignored if it is in the PROGRAM position. If Channel 2 Program/Execute switch 40 is in the EXECUTE position and Phase switch 42 is in the PROGRAM ENABLE position, a previously stored Channel 2 FES regimen will be executed while the Channel 1 FES regimen is being programmed.

A separate FES regimen for Channel 2 can be programmed in a similar manner. Channel 2 Program/Execute switch 40 is placed in the PROGRAM position, and Channel 1 Program/Execute switch 38 is placed in the EXECUTE position. The clinician then establishes the FES regimen by varying the setting of Channel 2 Amplitude potentiometer 32. The AMP2 signal from Channel 2 Amplitude potentiometer 32 is sampled by pulse generation circuit 16 when Channel 2 is in th PROGRAM mode, and a sequence of digital data based on the sequence of sampled values are stored for later use in reproducing the FES regimen for Channel 2 during the EXECUTE mode.

The EXECUTE mode has the lowest priority—in other words, pulse generation circuit 12 operates in the EXECUTE mode for a particular channel only when none of the other modes is active for that channel.

There are several possible combinations of outputs of Channel 1 and Channel 2 output circuits 18 and 20 during the EXECUTE mode. These are (1) Channel 1 output pulse train only; (2) synchronized Channel 1 and Channel 2 output pulse trains based upon the stored Channel 1 FES regimen; (3) sequential Channel 1 and Channel 2 output pulse trains both based upon the stored Channel 1 FES regimen; (4) Channel 2 output pulse train only based upon a stored Channel 2 FES regimen; and (5) a Channel 1 output pulse train based upon a stored Channel 1 FES regimen and a Channel 2 output pulse train based upon a stored Channel 2 FES regimen.

Channel 1 is placed in the EXECUTE mode when Channel 1 Program/Execute switch 38 is in the EXECUTE position. In this case, pulse generation circuit 12 produces the CH1 PULSE signal to Channel 1 output circuit 18. The pulse width of the CH1 PULSE signal is varied as a function of the sequence of digital data representing stored Channel 1 FES regimen, so as to replicate the variation in intensity of the output pulse train which occurred during the PROGRAM mode.

If Channel 2 Amplitude potentiometer 32 is in its minimum amplitude setting, no Channel 2 output is produced regardless of the position of Channel 2 Program/Execute switch 40 and Phase switch 42. in addition, no Channel 2 output is produced if Channel 1 Program/Execute switch 40 is in the EXECUTE position, Phase switch 42 is in the PROGRAM ENABLE position, and no Channel 2 FES regimen is stored.

The clinician may vary the amplitude of the Channel 1 output pulse train during the EXECUTE mode by changing the setting of Channel 1 Amplitude potentiometer 30. This allows the clinician to compensate for a different sensitivity which the patient may exhibit to the stored FES regimen from one visit to the next. This changed sensitivity can be the result of slightly different electrode placement or physiological changes of the patient.

During the EXECUTE mode, OFF/ON Ratio switch 44 is used to select the "time off" position of the FES regimen.

The rate of pulses produced during the EXECUTE mode is selectable by the clinician by means of Rate Select switch 26.

When Channel 1 and Channel 2 are both operated based upon the stored Channel 1 FES regimen, Channel 1 and Channel 2 Program/Execute switches 38 and 40 are placed in the "EXECUTE" position, and Phase switch 42 is placed in either the "SYNC" or the "180°" position. When Phase switch 42 is in the "SYNC" position, the CH1 PULSE and CH2 PULSE signals are identical and in phase. Both the CH1 PULSE and CH2

PULSE signals vary in pulse width as a function of the stored Channel 1 FES regimen. The amplitude of the Channel 1 output pulse train is determined by the AMP1 signal, and the amplitude of the Channel 2 output pulse train is determined by the AMP2 signal.

When Phase switch 42 is in the "180°" position, the CH2 PULSE signal from pulse generation circuit 12 is shifted in time so that it begins to "ramp up" after the CH1 PULSE signal has completed "ramp down". Both the CH1 PULSE and CH2 PULSE signals are based upon the same stored FES regimen. This shifting of the CH2 PULSE signal with respect to the CH1 PULSE signal is particularly effective when Channel 1 electrodes 22 and Channel 2 electrodes 24 are placed on the patient's body so that they sequentially activate different muscle groups which operate in different directions.

Operation of Channel 2 only in the EXECUTE mode is achieved when Channel 1 and Channel 2 Program-/Execute switches 38 and 40 are in the EXECUTE position, Phase switch 42 is in the PROGRAM ENABLE position, and Channel 1 Amplitude potentiometer 30 is at the minimum amplitude setting. The pulse width of the CH2 PULSE signal is varied as a function of a stored Channel 2 FES regimen. The amplitude of the output pulse train from Channel 2 output circuit 20 is controlled by the AMP2 signal.

The production of independent Channel 1 and Channel 2 output pulse trains based upon separately stored Channel 1 and Channel 2 FES regimens is achieved by placing switches 38 and 40 in their EXECUTE positions, and Phase switch 42 in the PROGRAM ENABLE position. The CH1 PULSE signal supplied by pulse generation circuit 16 to Channel 1 output circuit 18 has pulse widths which are based upon the stored sequence of digital data of the Channel 1 FES regimen; and the CH2 PULSE signal supplied by pulse generation circuit 16 to Channel 2 output circuit 20 has pulse widths which are based upon the stored sequence of digital data for the Channel 2 FES regimen. Providing different Channel 1 and Channel 2 output pulse trains is particularly advantageous when two different muscle groups are to be activated. For example, in one such application the Channel 1 output pulse train stimulates muscles which cause the patient's lower arm to be lifted, while the Channel 2 output pulse train stimulates muscles which cause the patient's hand to be moved in a particular manner.

The preferred embodiment of clinical device 10 shown in FIG. 1 is a fully functional, stand-alone unit which can be used by the clinician both to program and to execute an FES regimen. Clinical device 10 is preferably line-powered rather than battery-powered, since it is not intended for use by the patient.

Clinical device 10 is also capable of transferring the FES regimen program which has been established to personal device 12. Connection between clinical device 10 and personal device 12 is provided by connector 50. When personal device 12 is connected to connector 50, the clinician can initiate a transfer of the program stored by pulse generation circuit 16 through connector 50 to personal device 12 by actuating Program Transfer switch 46. This transfer of program includes the stored sample points produced during the program mode for each channel, together with the settings of Rate Select switch 26, Output Type switch 28, Phase Switch 42, and OFF/ON Ratio switch 44. This is all the data required by personal device 12 to replicate the program which has been created and stored within pulse generation circuit 16. Faulty transfer annunciator 54 provides an indication when a transfer has not been completed properly, so that the clinician knows when personal device 12 has received the data it needs to replicate the FES regimen. After the transfer has been successfully completed, personal device 12 can be disconnected from clinical device 10, and is capable of operating independently.

Personal device 12 shown in FIG. 2 is preferably a small, battery-operated, low cost microcomputer based device which replicates the FES regimen which was transferred from clinical device 10. In the embodiment shown in FIG. 2, personal device 12 includes connector 60, microcomputer circuitry 62, Channel 1 output circuit 64, Channel 2 output circuit 66, Channel 1 electrodes 68, Channel 2 electrodes 70, Channel 1 amplitude potentiometer 72, Channel 2 amplitude potentiometer 74, Continuous Mode switch 76, Remote switch 78, and battery power supply 80.

Connector 70 is a multi-lead connector which mates with connector 50 of clinical device 10 to provide data communication between pulse generation circuit 16 of clinical device 10 and microcomputer circuitry 62 of personal device 12.

Microcomputer circuitry 62 includes a microcomputer or microprocessor with associated read only memory (ROM) for operating program storage and random access memory (RAM) for data storage. When the FES regimen is transferred from clinical device 10 to personal device 12, it is in the form of digital data which is stored in RAM. The digital data includes the digital sample values needed to replicate the FES regimen for Channel 1 and Channel 2, together with data indicating the settings of Rate Select switch 26, Output Type switch 28, Channel 2 Phase switch 42, and OFF/ON Ratio switch 44.

Microcomputer circuitry 62 produces a CH1 PULSE signal which is supplied to Channel 1 output circuit 64 and a CH2 PULSE signal which is supplied to Channel 2 output circuit 66. The pulse rate of the CH1 PULSE signal and CH2 PULSE signals is determined by the data received from clinical device 10, which in turn was derived from the setting of Rate Select switch 26. The pulse widths of the CH1 PULSE and CH2 PULSE signals is based upon the stored digital sample values, and causes the intensity to vary in a manner which replicates the FES regimen.

Channel 1 output circuit 64 produces an output pulse train to Channel 1 electrodes 68 which is a function of the Channel 1 pulse signal from microcomputer circuitry 62 and an amplitude control signal from Channel 1 amplitude potentiometer 72. Similarly, Channel 2 output circuit 66 provides an output pulse train to Channel 2 electrodes 70 as a function of the Channel 2 pulse signal and an amplitude control signal from Channel 2 amplitude potentiometer 74. The output pulse trains are either monophasic or biphasic, depending upon the data from clinical device 10, which indicates the setting of Output Type switch 28.

Channel 1 and Channel 2 output circuits 64 and 66, therefore, operate in a manner which is essentially identical to Channel 1 and Channel 2 output circuits 18 and 20 of clinical device 10. Similarly, microcomputer circuitry 62 is capable of operating in a manner which is similar to the CONTINUOUS, REMOTE and EXECUTE modes of pulse generation circuit 16 of clinical device 10.

Continuous Mode switch 76 causes microcomputer circuitry 62 to produce a continuous output pulse train to Channel 1 output circuit 64 and Channel 2 output circuit 66. These output pulse trains are in-phase and identical in pulse width, and are continuous. The CONTINUOUS mode is used by the patient in determining the proper placement of electrodes 68 and 70.

Remote switch 78 provides a signal to microcomputer 62 which causes a REMOTE mode to be enabled. This REMOTE mode is similar to the remote mode provided by clinical device 10. As long as Remote switch 78 is actuated, output pulse trains are provided to Channel 1 and Channel 2 output circuits 64 and 66. When Remote switch 78 is released by the patient, the output pulse trains cease.

Personal device 12 is battery powered by battery power supply 80. Power is supplied to microcomputer circuitry 62, even when personal device 12 is not in use, in order to maintain the stored FES regimen within RAM of microcomputer 62.

A faulty data transfer between clinical device 10 and personal device 12 is identified by a predetermined signal (or absence of a predetermined response signal) transmitted by microcomputer circuit 62 through connector 60 and connector 50 to pulse generation circuit 16. This causes faulty transfer annunciator 54 of clinical device 10 to be actuated. The clinician can then again attempt a transfer by actuating Program Transfer switch 46.

Clinical device 10 of the present invention is also capable of receiving previously stored programs from external memory module 14 thorugh connector 52 and for transferring a program which has been created and stored from pulse generation circuit 16 to external memory module 14. Load/Save switch 48 (which in some embodiments includes multiple switches) allows the clinician to decide whether a previously stored FES regimen will be loaded from external memory module 14 to pulse generation circuit 16, or whether the program which has been created and stored in pulse generation circuit 16 will be saved by transferring it to external memory module 14. In preferred embodiments, Load/Save switch 48 also permits the operator to initiate the Load or Save operation.

In the embodiment shown in FIG. 3, external memory module 14 includes connector 90, memory 92, and battery backup circuit 94. Memory 92 is, in this embodiment, a read/write random access memory. The contents of memory 92 are maintained, even when external memory module 14 is not in use, by power from battery backup circuit 94.

Connector 90 is a multi-terminal connector which mates with connector 52 of clinical device 10. When Load/Save switch 48 is in the load setting and is actuated, the contents of memory 92 are transferred through connector 90 and connector 52 to pulse generation circuit 16. In this way, a previously stored FES regimen contained within memory 92 is transferred to pulse generation circuit 16. This loading of the regimen into clinical device 10 does not destroy the contents of memory 92.

When an FES regimen has been established during the PROGRAM mode, the clinican can save that FES regimen in external memory module 12 by placing Load/Save switch 48 in the Save setting and actuating it. This causes the data representing the FES regimen to be transferred from pulse generation circuit 16 into memory 92. This data includes the digital sample data, as well as settings of Rate Select switch 26, Output Type switch 28, Phase switch 42, and OFF/ON Ratio switch 44.

After the FES regimen has been saved in external memory module 124, connectors 90 and 52 can be disconnected, and clinical device 10 can be used again to establish an FES regimen for another patient. External memory module 14 is preferably a small enclosed device with no user controls. When not in active use, external memory module 14 can be stored remotely by the clinician.

With the system of the present invention, therefore, the clinican establishes an FES regimen using clinical device 10. Once the FES regimen has been established, the clinician transfers the established FES regimen to the patient's personal device 12.

Once the FES regimen has been transferred to personal device 12, the patient can continue to use personal device 12, and each time it will recreate the same FES regimen. The clinician can let the patient follow the stimulation schedule without fear of losing the FES regimen is having it altered for any reason. The personal device 12 has only amplitude controls 72 and 74 and Continuous Mode switch 76 and Remote switch 78 as its user controls. The patient cannot, therefore, modify the FES regimen in any way.

The clinican also preferably loads the FES regimen which has been established into an external memory module 14, and stores that external memory module 14 until the patient's next visit.

The next time the patient visits the clinician, the previously established FES regimen can be recalled in exact form by reconnecting the external memory module 14 for that patient and transferring the FES regimen into pulse generation 16 of clinical device 10. The clinician can then place clinical device 10 in the EXECUTE mode, and observe how the patient is reacting to the previously established FES regimen. If a change in a regimen is required, clinical device 10 is placed in the PROGRAM mode, and a new FES regimen is established. That new FES regimen is then transferred to personal device 12, to replace the previously stored FES regimen in microcomputer circuitry 62, and is transferred to the external memory module 14 of that patient, to replace the previously stored FES regimen.

With the present invention, therefore, the patient has all the advantages of a programmable FES device, without the increased cost and size which normally would be required for those features. This is achieved by the use of a more complex clinical device 10, which can be line-powered, rather than battery-powered, and which has a number of switches and controls which are useful to the clinician, but are not of importance to the patient's use at home. The cost of switches and other operator controls is a major component in the overall cost of any FES device, and therefore, the present invention permits a fully programmable, yet low cost personal device 12 to be provided to the patient.

Although the present invention has been described with reference to preferred embodiments, workers skilled in the art will recognize that changes may be made in form and detail without departing from the spirit and scope of the invention.

What is claimed is:

1. A functional electrical stimulation (FES) system for providing an electrical output pulse train which is applied to a patient's body to cause a desired FES regimen of contraction and relaxation of muscles of the patient, the FES system including:

a clinical FES device for creating the desired FES regimen, the clinical FES device including:
- means for producing a clinical device output pulse train;
- means for applying the clinical device output pulse train to the patient's body;
- means for selecting a program mode of operation during which the desired FES regimen is established;
- means for providing an intensity control signal during the program mode;
- means for controlling the intensity of the clinical device output pulse train during the program mode as a function of the intensity control signal;
- means for storing, during the program mode, a sequence of digital data as a function of the intensity control signal, the stored sequence being representative of the desired FES regimen; and a personal FES device for producing a personal device output pulse train in accordance with the desired FES regimen, the personal FES device including:
- means for receiving, from the clinical FES device, the stored sequence of digital data representative of the desired FES regimen;
- means for storing the digital data;
- means for producing a personal device output pulse train;
- means for applying the personal device output pulse train to the patient's body; and
- means for controlling the intensity of the personal device output pulse train as a function of the digital data to reproduce the desired FES regimen.

2. The FES system of claim 1 wherein the clinical FES device further includes:
- means for selecting an execute mode of operation during which the desired FES regimen is reproduced; and
- means for controlling the intensity of the output pulse train of the clinical FES device during the execute mode as a function of the stored sequence of digital data.

3. The FES system of claim 2 wherein the clinical device further includes:
- means for connecting the clinical FES device and the personal FES device; and
- means for initiating a transfer of the stored sequence of digital data from the clinical FES device to the personal FES device.

4. The FES system of claim 1 and further including:
- an external read/write memory unit for storing data; and
- wherein the clinical FES device includes means for connecting the clinical device and the external read/write memory unit to permit transferring of digital data between the clinical FES device and the external read/write memory unit.

5. The FES system of claim 4 wherein the clinical FES device further includes:
- means for loading data from the external read/write memory unit into the means for storing a sequence of digital data during a load operation, the data from the external read/write memory unit representing a prerecorded FES regimen; and
- means for transferring digital data from the means for storing a sequence of digital data to the external read/write memory unit during a save operation, the digital data representing the desired FES regimen.

6. The FES system of claim 1 wherein the clinical FES device further includes means for selecting a pulse rate of the clinical device output pulse train during the program mode; and wherein the personal FES device further includes means for controlling pulse rate of the personal device output pulse train as a function of the pulse rate selected by the means for selecting.

7. A functional electrical stimulation (FES) system including:

a clinical FES device including:
- means for producing a clinical device output signal;
- means for applying the clinical device output signal to a patient's body to cause contraction of muscles;
- means for varying intensity of the clinical device output signal with time during a program mode to produce a desired FES regimen;
- means for periodically sampling a signal representative of the intensity during the program mode;
- means for storing digital data based upon the periodic sampling;
- means for transferring the digital data; and a personal FES device including:
- means for producing a personal device output signal;
- means for applying the personal device output signal to the patient's body to cause contraction of muscles;
- means for storing the digital data transferred from the clinical FES device; and
- means for varying the intensity of the personal device output signal with time as a function of the stored digital data to reproduce the desired FES regimen.

8. The FES system of claim 7 wherein the clinical FES device further includes:
- means for selecting an execute mode of operation during which the desired FES regimen is reproduced; and
- means for controlling the intensity of the clinical device output signal during the execute mode as a function of the digital data.

9. The FES system of claim 8 wherein the clinical FES device further includes:
- means for connecting the clinical FES device and the personal FES device; and
- means for initiating a transfer of the digital data from the clinical FES device to the personal FES device.

10. The FES system of claim 7 and further including:
- an external read/write memory unit for storing data; and
- wherein the clinical FES device includes means for connecting the clinical device and the external read/write memory unit to permit transferring of digital data between the clinical FES device and the external read/write memory unit.

11. The FES system of claim 10 wherein the clinical FES device further includes:
- means for loading data from the external read/write memory unit into the means for storing digital data during a load operation, the data from the external read/write memory unit representing a prerecorded FES regimen; and means for transferring digital data from the means for storing digital data to the external read/write memory unit during a save operation, the digital data representing the desired FES regimen.

12. The FES system of claim 7 wherein the clinical FES device further includes means for selecting a pulse rate of the clinical device output signal during the program mode; and wherein the personal FES device further includes means for controlling pulse rate of the personal device output signal as a function of the pulse rate selected by the means for selecting.

13. For use in conjunction with a clinical functional electrical stimulation (FES) device which creates a desired FES regimen by applying a clinical device output signal to a patient's body, controlling intensity of the clinical device output signal during a program mode, and storing digital data representative of intensity as a function of time; a personal FES device for producing a personal device output signal which replicates the desired FES regimen, the personal FES device including:
  means for receiving, from the clinical FES device, the digital data;
  means for storing the digital data;
  means for producing the personal device output signal;
  means for applying the personal device output signal to the patient's body; and
  means for varying the intensity of the personal device output signal with time as a function of the stored digital data to reproduce the desired FES regimen.

14. A functional electrical stimulation (FES) system for causing a desired FES regimen of contraction and relaxation of muscles of a patient, the system including:
  a clinical FES device for creating the desired FES regimen, the clinical FES device including:
    first clinical device channel amplitude amplitude control means for providing a first clinical device amplitude control signal;
    first program/execute select means for selecting between a first program mode of operation and a first execute mode of operation;
    pulse rate select means for selecting a a pulse repetition rate;
    means for periodically sampling the first clinical device amplitude control signal during the first program mode to produce a sequence of first sample values;
    means for storing a sequence of first digital data based upon the first sample values during the first program mode;
    first clinical device pulse generation means for generating a first clinical device pulse signal at the selected pulse repetition rate, the first clinical device pulse signal having a constant pulse width during the first program mode of operation and having a pulse width which varies as a function of the stored sequence of first digital data during the first execute mode of operation;
    first clinical device channel output means for providing a first clinical device output pulse train for application to the patient's body, the first clinical device output pulse train having an amplitude which is a function of the first amplitude control signal and having a pulse width which is a function of the pulse width of the first pulse signal; and
    means for transferring the selected pulse repetition rate and the first digital data during a transfer operation;
  a personal FES device for reproducing the desired FES regimen, the personal FES device including:
    means for storing the selected pulse repetition rate and the sequence of first digital data received from the clinical FES device during the transfer operation;
    first personal device channel amplitude control means for providing a first personal device amplitude control signal;
    first personal device pulse generation means for generating a first personal device pulse signal at the selected pulse repetition rate, the first personal device pulse signal having a pulse width which varies as a function of the sequence of first digital data; and
    first personal device channel output means for providing a first personal device output pulse train for application to the patient's body, the first personal device output pulse train having an amplitude which is a function of the first personal device amplitude control signal and having a pulse width which is a function of the pulse width of the first personal device pulse signal.

15. The FES system of claim 14 wherein the clinical device further includes:
  second clinical device channel amplitude control means for providing a second clinical device amplitude control signal;
  second program/execute select means for selecting between a second program mode of operation and a second execute mode of operation;
  means for periodically sampling the second clinical device amplitude control signal during the second program mode to produce a sequence of second sample values;
  means for storing a sequence of second digital data based upon the second sample values during the program mode;
  second clinical device pulse generation means for generating a second clinical device pulse signal at the selected pulse repetition rate, the second clinical device pulse signal having a constant pulse width during the second program mode of operation and having a pulse width which varies as a function of the stored sequence of second digital data during the second execute mode of operation;
  second clinical device channel output means for providing a second clinical device output pulse train for application to the patient's body, the second clinical device output pulse train having an amplitude which is a function of the second amplitude control signal and having a pulse width which is a function of the pulse width of the second pulse signal; and
  means for tansferring the second digital data during the transfer operation; and
wherein the personal FES device further includes:
  means for storing the sequence of second digital data received from the clinical FES device during the transfer operation;
  second personal device channel amplitude control means for providing a second personal device amplitude control signal;
  second personal device pulse generation means for generating a second personal device pulse signal at the selected pulse repetition rate, the second pulse signal having a pulse width which varies as a function of the stored sequence of second digital data; and second personal device channel output means for providing a second personal device output pulse train for application to the patient's body, the second personal device output pulse train having an amplitude which is a function of the second personal device amplitude control signal and having a pulse width which is a function of the pulse width of the second personal device pulse signal.

16. A method of creating with a clinical functional electrical stimulation (FES) device and a desired FES regimen of contraction and relaxation of muscles of a patient, and subsequently reproducing the desired FES regimen with a separate personal FES device, the method including:

applying, with the clinical FES device, an electrical signal to a patient's body;

varying intensity of the electrical signal with time to produce a desired FES regimen;

periodically sampling a signal representative of the intensity;

storing in the clinical FES device digital data based upon the periodic sampling which represents the FES regimen;

transferring the digital data from the clinical FES device to the personal FES device; and applying to the patient's body an electrical output signal generated by the personal FES device which varies in intensity with time as a function of the digital data to reproduce the FES regimen.

17. For use in conjunction with a personal functional electrical stimulation (FES) device which reproduces a desired FES regimen by receiving a stored sequence of digital data representative of the FES regimen, storing the digital data, producing a personal device output pulse train, and controlling intensity of the personal device output pulse train as a function of the stored data; a clinical FES device for creating the desired FES regimen, the clinical FES device including:

means for producing a clinical device output pulse train;

means for applying the clinical device output pulse train to a patient's body;

means for selecting a program mode of operation during which the desired FES regimen is established;

means for providing an intensity control signal during the program mode;

means for controlling the intensity of the clinical device output pulse train during the program mode as a function of the intensity control signal; and means for storing, during the program mode, a sequence of digital data as a function of the intensity control signal, the stored sequence being representative of the desired FES regimen.

* * * * *